United States Patent [19]
Karell

[11] Patent Number: 5,792,067
[45] Date of Patent: Aug. 11, 1998

[54] APPARATUS AND METHOD FOR MITIGATING SLEEP AND OTHER DISORDERS THROUGH ELECTROMUSCULAR STIMULATION

[76] Inventor: Manuel L. Karell, 3573 22nd St., San Francisco, Calif. 94114

[21] Appl. No.: 615,094

[22] Filed: Mar. 13, 1996

Related U.S. Application Data

[60] Provisional application No. 60/007,393, Nov. 21, 1995.

[51] Int. Cl.$^6$ .............. A61B 5/08; A61B 5/04; A61N 1/372
[52] U.S. Cl. .............. 600/534; 600/545; 128/848; 607/42; 607/134
[58] Field of Search .............. 128/639, 642, 128/721, 724, 733, 777, 905, 848, 207.15; 607/42, 44–48, 60–61, 72–74, 134–135; 600/23–24, 26–27, 534, 545; 602/902

[56] References Cited

U.S. PATENT DOCUMENTS

| | | | |
|---|---|---|---|
| 3,480,010 | 11/1969 | Crossley | 128/132 |
| 3,522,811 | 8/1970 | Schwartz et al. | |
| 4,153,060 | 5/1979 | Korostoff et al. | |
| 4,310,002 | 1/1982 | Takinishi et al. | 128/642 |
| 4,519,400 | 5/1985 | Brenman et al. | 128/741 |
| 4,637,405 | 1/1987 | Brenman et al. | |
| 4,644,330 | 2/1987 | Dowling | 340/575 |
| 4,669,459 | 6/1987 | Spiewak et al. | 128/136 |
| 4,715,367 | 12/1987 | Crossley | 128/724 X |
| 4,788,533 | 11/1988 | Mequignon | 340/575 |
| 4,830,008 | 5/1989 | Meer | 128/721 |
| 4,901,737 | 2/1990 | Toone | 128/848 |
| 4,907,602 | 3/1990 | Sanders | |
| 4,924,880 | 5/1990 | O'Neill et al. | 128/787 |
| 4,944,310 | 7/1990 | Sullivan | 128/848 |
| 5,042,506 | 8/1991 | Liberati | 128/848 |
| 5,123,425 | 6/1992 | Shannon, Jr. et al. | 128/848 |
| 5,146,918 | 9/1992 | Kallok et al. | |
| 5,178,156 | 1/1993 | Takishima et al. | |
| 5,190,053 | 3/1993 | Meer | 128/787 |
| 5,207,231 | 5/1993 | Fakhri | |
| 5,284,161 | 2/1994 | Karell | 128/848 |
| 5,330,527 | 7/1994 | Montecalvo et al. | 607/152 |
| 5,427,096 | 6/1995 | Bogusiewicz et al. | 128/639 |
| 5,591,216 | 1/1997 | Testerman et al. | 128/716 X |

FOREIGN PATENT DOCUMENTS

| | | | |
|---|---|---|---|
| 1553140 | 3/1990 | U.S.S.R. | 128/787 |
| 5005278 | 12/1985 | WIPO | |

OTHER PUBLICATIONS

Herbert Paskow and Sanford Paskow, "Dentistry's Role in Treating Sleep Apnea and Snoring," New Jersey Medicine, vol. 88, No. 11, Nov. 1991, pp. 815–817.

Journal of Dental Research, Abstracts of Papers, 7th General Session and Exhibition of the International Association for Dental Research, Mar. 13–17, 1996, San Francisco, CA, vol. 75, Special Issue (1996).

Reissue Application Serial No. 08/598,203, filed Feb. 7, 1996, entitled Snopper-The Snoring Stopper Anti–Snoring Mouth Device corresponding to U.S. Pat. No. 5,284,161 issued Feb. 8, 1994 to Karell.

*Primary Examiner*—Francis Jaworski
*Attorney, Agent, or Firm*—Reed Smith Shaw & McClay LLP

[57] ABSTRACT

An electromuscular stimulator that effects a beneficial medical purpose selected from the group consisting of mitigating snoring, mitigating obstructive sleep apnea, mitigating hypertension, dental analgesia, general analgesia, monitoring physiological conditions and facilitating the intraoral delivery of medication is disclosed. The electromuscular stimulator includes a first electrode for making electrical contact with a first anatomical structure selected from the group consisting of a hard palate, a soft palate and a pharynx; a second electrode for making electrical contact with a second anatomical structure; a control unit operably connected to the first and second electrodes; and a means for positioning the first and second electrodes relative to the first and second anatomical structures, respectively.

57 Claims, 5 Drawing Sheets

APPARATUS AND METHOD FOR MITIGATING SLEEP AND OTHER DISORDERS THROUGH ELECTROMUSCULAR STIMULATION

RELATED APPLICATION

This application is a claiming the benefit under 35 U.S.C. 119(e) of U.S. Provisional application Ser. No. 60/007,393, filed Nov. 21, 1995.

TECHNICAL FIELD

The present invention relates to the mitigation of sleep and other disorders and, more particularly, to an apparatus and method of mitigating such disorders through electromuscular stimulation.

BACKGROUND

Obstructive sleep apnea ("OSA") and snoring are closely related sleep breathing disorders. The vibration of relaxed throat muscles of a sleeping individual during respiration causes snoring. Similarly, relaxed airway and tongue muscles, which obstruct respiratory air flow during sleep, cause OSA.

Others have proposed a variety of devices for alleviating OSA and snoring. A first approach is to utilize mechanical means. One device applies mechanical pressure to the soft palate to prevent vibration. See Spiewak et al., ANTI-SNORING DEVICE, U.S. Pat. No. 4,669,459, issued Jun. 2, 1987. Another device mechanically forces the mouth into an open position. See Toone, METHOD AND THERAPEUTIC APPARATUS FOR REDUCING SNORING, U.S. Pat. No. 4,901,737, issued Feb. 20, 1990. Some devices utilize mechanical means to keep the tongue protruded. See, e.g., Herbert Paskow & Sanford Paskow, "Dentistry's Role in Treating Sleep Apnea and Snoring," New Jersey Medicine, Vol. 88, No. 11, November 1991.

A second approach is to use a feedback mechanism to condition the sleeper. Some devices detect the presence of snoring and then generate an aversive audio signal in response thereto to deter the user from snoring. See, e.g., Dowling, ANTI-SNORING DEVICE, U.S. Pat. No. 4,644,330, issued Feb. 17, 1987; Mequignon, DEVICE FOR INTERRUPTING THE SNORING OF A SLEEPING PERSON, U.S. Pat. No. 4,788,533, issued Nov. 29, 1988. Another device detects the presence of snoring and in response thereto delivers an electrical shock to condition the sleeper against snoring. See Crossley, ELECTRONIC SNORE DEPRESSOR, U.S. Pat. No. 3,480,010, issued Nov. 25, 1969.

Other approaches include the use of (1) mechanical means to retrain and retone intraoral muscles, see Liberati, ANTI-SNORING TRAINING DEVICE, U.S. Pat. No. 5,042,506, issued Aug. 27, 1991; (2) continuous positive air pressure ("CPAP") to maintain patentcy of the upper airway, see, e.g., Sullivan, DEVICE FOR TREATING SNORING SICKNESS, U.S. Pat. No. 4,944,310, issued Jul. 31, 1990; and (3) sublingual electrical stimulation to cause the tongue to move anteriorly, see Meer, METHOD AND APPARATUS FOR ELECTRICAL SUBLINGUAL STIMULATION, U.S. Pat. No. 5,190,053, issued Mar. 2, 1993.

Most of these prior approaches have proven to be ineffective for their intended purpose and, therefore, have not been commercialized. Indeed, none of the prior approaches that utilize electrical stimulation have proven to be effective. Most, if not all, of these electrical stimulation devices require that electrodes be implanted into an anatomical structure prior to operation. Such an approach requires a surgical procedure and, thus, a large financial investment before it can be determined whether the device will work for an intended user. Moreover, the implantation, a surgical procedure, is painful for the intended user.

SUMMARY OF THE INVENTION

The current invention provides an electromuscular stimulator that effects a beneficial medical purpose selected from the group consisting of mitigating snoring, mitigating obstructive sleep apnea, mitigating hypertension, dental analgesia, general analgesia, monitoring physiological conditions and facilitating the intraoral delivery of medication. This is accomplished without incurring the above-mentioned drawbacks of the prior art.

The electromuscular stimulator includes a first electrode for making electrical contact with a first anatomical structure selected from the group consisting of a hard palate, a soft palate and a pharynx; a second electrode for making electrical contact with a second anatomical structure; a control unit operably connected to the first and second electrodes; and a means for positioning the first and second electrodes relative to the first and second anatomical structures, respectively.

The advantages of the present electromuscular stimulator over conventional devices are numerous and include the following, without limitation: (1) enhanced effectiveness; (2) does riot require implantation of electrodes; (3) does not require a large financial investment to determine the effectiveness of the device for a given user; (4) permits greater mobility and, therefore, comfort for the user; and (5) can be custom fit by the user, without the costly intervention of a third party, e.g., a dentist.

DESCRIPTION OF THE PREFERRED EMBODIMENT

Figure 1:
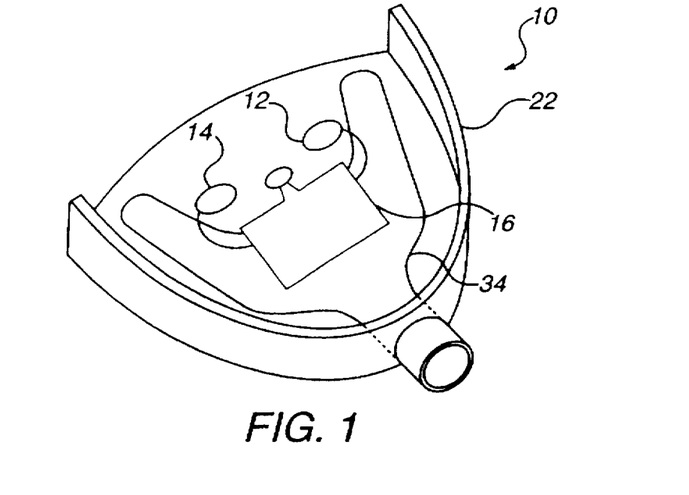
FIG. 1 is a plan view of a substantially intraoral embodiment of the present invention.

FIG. 1 depicts an intraoral electromuscular stimulator 10. Stimulator 10 comprises a first electrode 12 for making electrical contact with a first anatomical structure. The first anatomical structure can be any of a number of intraoral anatomical structures, including the hard palate, soft palate or pharynx.

Stimulator 10 further comprises a second electrode 14 for making electrical contact with a second anatomical structure. The second anatomical structure can be any of a number of anatomical structures, as long as a voltage applied between the first and second anatomical structures causes a current to flow through the first anatomical structure. The goal is to effect current flow through the first anatomical structure. In some cases, the voltage necessary to effect such current flow will be less if the first electrode 12 and the second electrode 14 are applied to the same anatomical structure, i.e., the first and second anatomical structures are the same. In FIG. 1, the first electrode 12 and second electrode 14 are positioned so that both electrodes are applied to the soft palate so that current flow is achieved in the soft palate.

For both first electrode 12 and second electrode 14, electrical contact between electrode 12 or 14 and the corresponding anatomical structure can be effected by merely positioning electrode 12 or 14 adjacent to the corresponding anatomical structure or by implanting electrode 12 or 14 into the corresponding anatomical structure. It is not even necessary for electrode 12 or 14 to be directly touching the corresponding anatomical structure to effect electrical contact if there is a layer of saliva between electrode 12 or 14 and the corresponding anatomical structure because saliva can act as an electroconductor. Preferably, electrode 12 or 14 is placed adjacent to and in direct contact with the corresponding anatomical structure.

First electrode 12 and second electrode 14 can be made of any electroconductive material that is suitable for the intraoral environment. Both electrodes need not be made of the same material. Suitable materials include, without limitation, metal, carbon-impregnated metal, carbon-impregnated plastic, electroconductive rubber and electroconductive gels. Current flow through carbonimpregnated electroconductive materials is more diffuse relative to current flow in other electroconductors. This property can be utilized to advantage by making carbonimpregnated electrodes that enhance the effectiveness of the stimulator and, at the same time, result in less pain to the user and less trauma, e.g., burning, to adjacent tissue. Preferably, each electrode 12 or 14 is pliable so that it can be molded to fit the contours of the corresponding anatomical structure, e.g., the concavity of the roof of the mouth.

Figure 2:
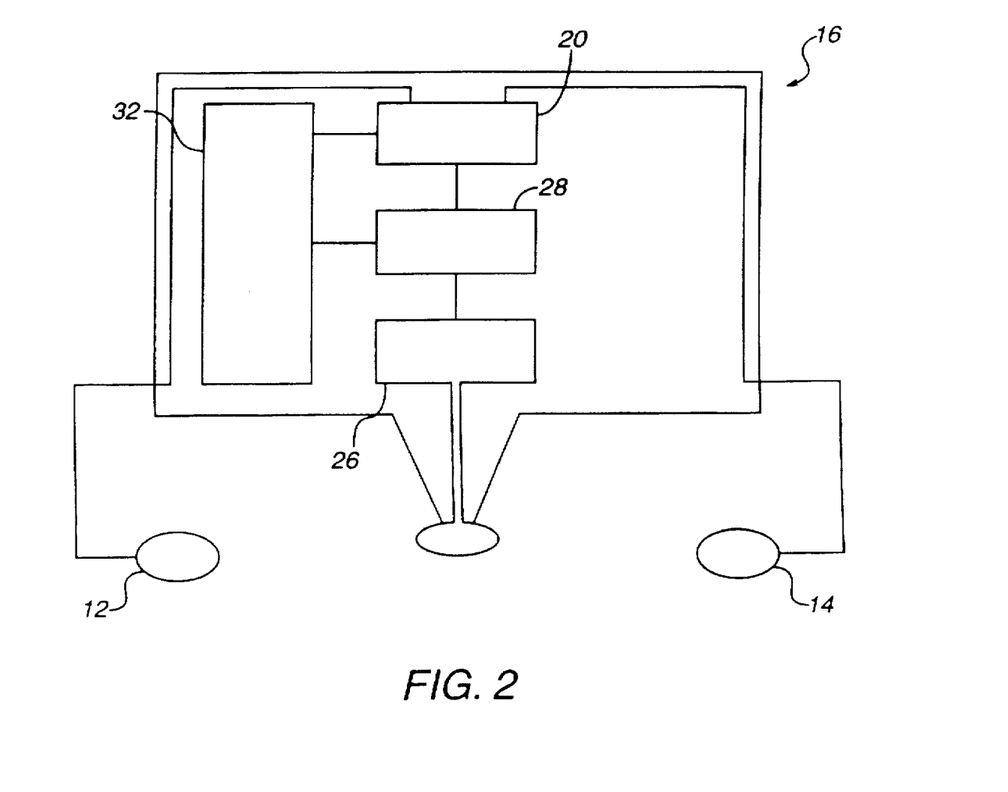
FIG. 2 is a schematic cross-section of an intraoral control unit for a substantially intraoral embodiment of the present invention.

In a first embodiment, stimulator 10 further comprises an intraoral control unit 16. FIG. 2 is a schematic diagram, which depicts internal components of intraoral control unit 16. Referring to FIG. 2, intraoral control unit 16, at a minimum, contains an electrical signal generator 20, which is operably connected to first electrode 12 and second electrode 14. Generator 20 is responsible for applying a voltage between first electrode 12 and second electrode 14.

Utilizing currently-available integrated circuit technology or other technologies, some yet to be discovered, intraoral control unit 16 and its internal components, e.g., generator 20 and the other internal components discussed below, can be microminiaturized or sized to fit within the mouth of the user during operation. In this way the comfort of the user is increased because stimulator 10 can be made small enough for the user to close his mouth completely after inserting stimulator 10 into his mouth. Moreover, the mobility and, therefore, comfort and safety of the user is increased because there is no need for the user to be tethered to an extraoral unit, e.g., a bedside unit, during operation. Where intraoral control unit 16 is designed to be placed in the mouth, it may be desirable to hermetically seal intraoral control unit 16 or the components contained therein so that the user's saliva does not short out the internal components or damage them in some other way. A hermetically-sealed intraoral control unit 16 would also prevent leakage from inside intraoral control unit 16 of chemicals or other substances that might pose a health hazard to the user.

Electrical signal generator 20 preferably comprises a pulse generator 20, e.g., a transcutaneous electrical nerve stimulator, that comprises a digital integrated circuit. Electrical signal generator 20 should be capable of generating a variety of waveforms, including pulses, having a variety of characteristics, including shapes, amplitudes and frequencies. Electrical signal generator 20 should be further capable of operating in both intermittent and constant modes, i.e., generating both intermittent and constant signals. Optionally, the characteristics of the signal can be controlled by the clinician and/or user.

Under some circumstances, it may be desirable for stimulator 10 to be able to predict or detect the onset of a physiological condition and, in response, generate an appropriate electrical signal that effects a beneficial medical purpose. To this end, intraoral control unit 16 further may comprise a sensor 26 that is capable of detecting the presence of a physiological condition, e.g., a condition that is a precursor to the onset of sleep apnea or the onset of sleep apnea itself. Depending on its nature, sensor 26 may reside either inside or outside the mouth of the user. Any of a variety of sensors 26 can be used, including, without limitation, electrodes that monitor activity in the brain; electrodes that monitor electrical activity in an intraoral muscle; a chemical sensor that monitors an intraoral level of a gas, e.g., $CO_2$, $O_2$ or any hydrocarbon emitted from tissue; a force gauge, e.g., a strain gauge or pressure transducer, that monitors the tone of an intraoral muscle; an air flow sensor that monitors intraoral air flow; and a microphone that monitors intraoral sounds, e.g., that of snoring.

If intraoral control unit 16 comprises a sensor 26, it should further comprise a controller 28 that is operably connected to sensor 26 and operably connected to electrical signal generator 20 for activating electrical signal generator 20 in response to detection of the physiological condition. Controller 28 is responsible for interpreting the output of sensor 26 in terms of the existence or nonexistence of a physiological condition, determining whether the generation of an electrical signal is warranted, ascertaining appropriate characteristics for any such electrical signal and activating electrical signal generator 20 to produce such an electrical signal with such characteristics. Controller 28 can be a mechanical, chemical or electrical device. If electrical, it could be either analog or digital. If digital, it could be a programmable microprocessor or hardwired digital circuitry capable of performing logical operations. If a microprocessor is used, an expert system could be installed in the microprocessor to perform the required functions, e.g., interpretation of output from sensor 26. In sum, any of a multitude of controller types could be used, some known and some yet to be discovered.

Intraoral control unit 16 further may comprise a power supply 32. Power supply 32 preferably is microminiaturized and hermetically sealed. Power supply 32 may be chemical-based, e.g., a battery, or based on some other type of energy source, e.g., electrical current from an external wall socket.

Referring to FIG. 1, stimulator 10 further comprises a positioning means 22 for positioning the first and second electrodes relative to the first and second anatomical structures, respectively. Positioning means 22 can have any of a variety of shapes, including, e.g., that of a denture-like plate, as depicted in FIG. 1. In FIG. 1, first electrode 12 and second electrode 14 are operably connected to intraoral control unit 16, which in turn is attached, either fixedly or removably, to positioning means 22. In alternative embodiments, electrodes 12 and 14 might be directly attached to positioning means 22, as in, e.g., FIG. 3. A variety of configurations are possible.

Figure 3:
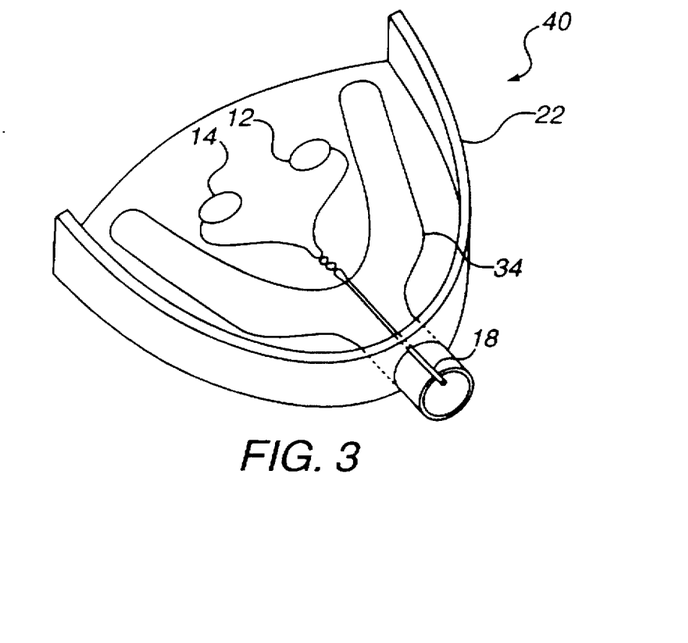
FIG. 3 is a plan view of a substantially extraoral embodiment of the present invention.

Positioning means 22 is designed to attach, either fixedly or removably, to a third anatomical structure, e.g., the palate and/or the teeth of the user, so that the first and second electrodes 12 and 14 are maintained in a fixed spatial relationship with the first and second anatomical structures, respectively. Positioning means 22 can be implanted into the third anatomical structure to effect a fixed connection therebetween. Alternatively, positioning means 22 can be removably attached to the third anatomical structure with any of a variety of connecting means, including, without limitation, an adhesive, a clamping device or a device utilizing suction. In FIGS. 1 and 3, positioning means 22 is a denture-like plate that can be removably attached to the upper teeth and palate in a conventional manner.

To reduce the cost of fitting positioning means 22 to the third anatomical structure, it, optionally, can be constructed of a material that becomes moldable when heated, e.g., by immersion in a hot water bath, for a period of time and hardens upon cooling. In this way, the user can heat positioning means 22; mold it into a desired shape, e.g., by inserting it into the mouth and pressing it against the third anatomical structure until a desired shape is attained; and cooling positioning means 22 until it hardens into the desired shape, without paying a third party, e.g., a physician, to custom fit positioning means 22. Moreover, positioning means 22 can be a reusable, cleanable device or a disposable device.

Referring to FIG. 1, stimulator 10 further may comprise an air channel 34 to reduce obstructive air flow due to the placement of stimulator 10 within the mouth of the user. Air channel 34 should be operably connected to positioning means 22 and should have an intraoral end and an extraoral end to promote the free flow of air around stimulator 10 and between the lungs of the user and an external air source, e.g., the ambient atmosphere. In FIG. 1, air channel 34 comprises two tubes towards the back of the throat that merge into one tube, which projects from the mouth of the user.

Figure 4:
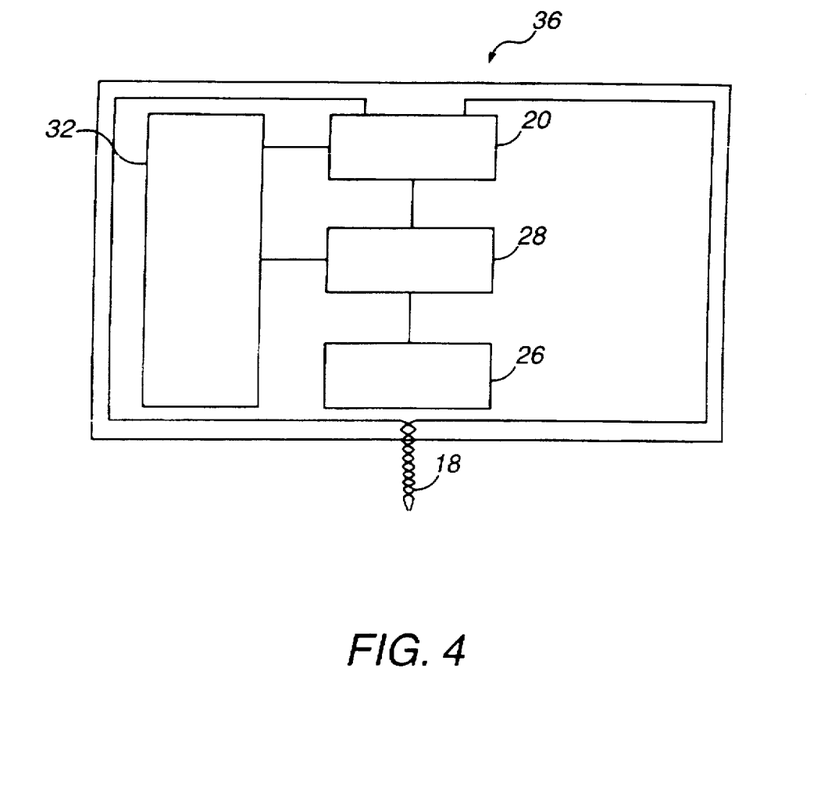
FIG. 4 is a schematic cross-section of an extraoral control unit for a substantially extraoral embodiment of the present invention.
Figure 5:
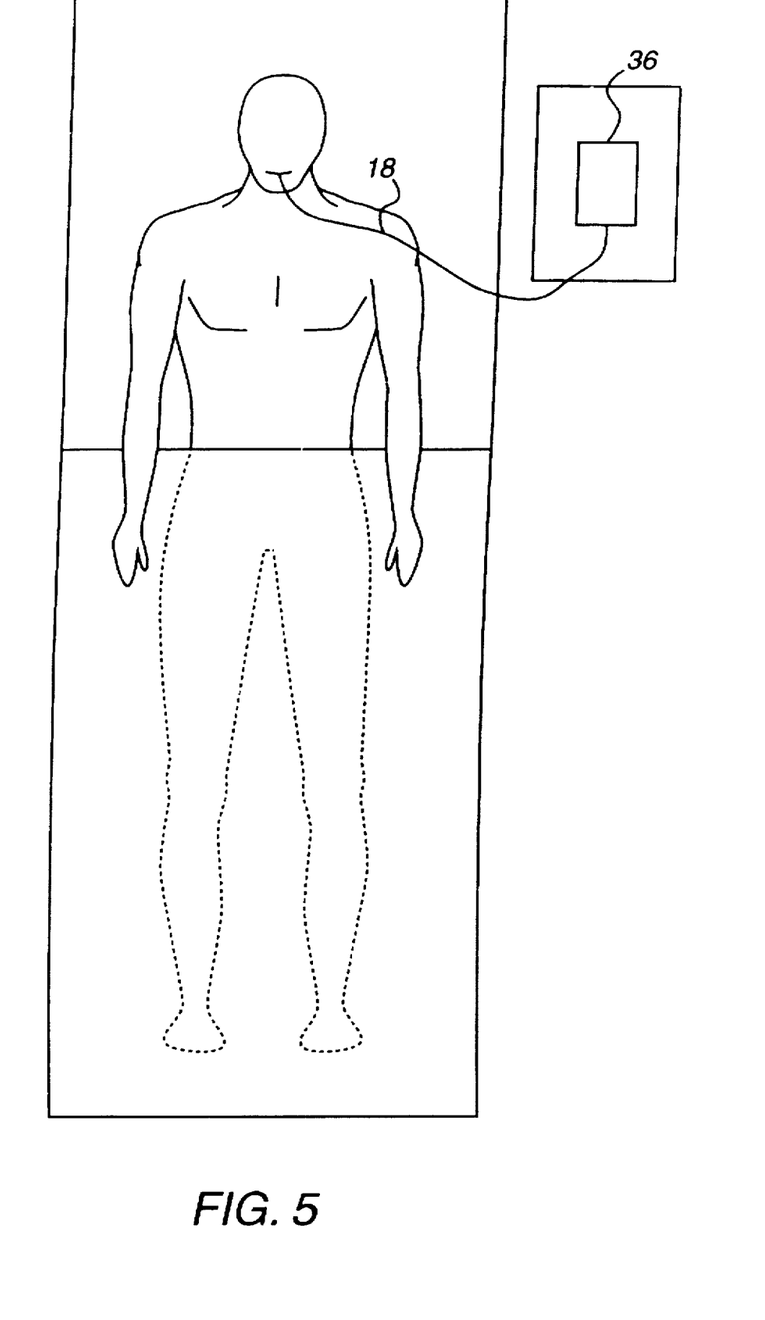
FIG. 5 illustrates one way in which a substantially extraoral embodiment of the present invention might be configured.

In a second embodiment, all of the functionality provided by intraoral control unit 16 in the first embodiment is implemented in an extraoral control unit 36, an entirely extraoral unit, e.g., a unit that is mounted on a belt and worn around the waist or a bedside unit, as shown in FIG. 5. In this embodiment, the stimulator comprises a mouthpiece unit 40, as depicted in FIG. 3; extraoral control unit 36, as depicted in FIGS. 4 and 5; and a communication element 18, as depicted in FIGS. 4 and 5. Extraoral control unit 36 is operably connected to first electrode 12 and second electrode 14 by way of communication element 18, e.g., a coaxial cable.

The above description of the internal components of intraoral control unit 16 in the first embodiment applies equally to the internal components of extraoral control unit 36 in this embodiment, with the exception that the constraints of miniaturization and compatibility with the intraoral environment are eliminated. Accordingly, utilization of an entirely extraoral unit can reduce the cost of manufacture, permit an increase in the sophistication of extraoral control unit 36 relative to intraoral control unit 16, reduce obstructive air flow and provide greater room for the tongue by obviating the placement of intraoral control unit 16 and achieve other advantages, some yet to be discovered. Utilization of an entirely extraoral unit, moreover, can facilitate modification of the control circuitry, where necessary, and reduce the risk of misplacing an otherwise expensive miniature dental appliance.

Figure 6:
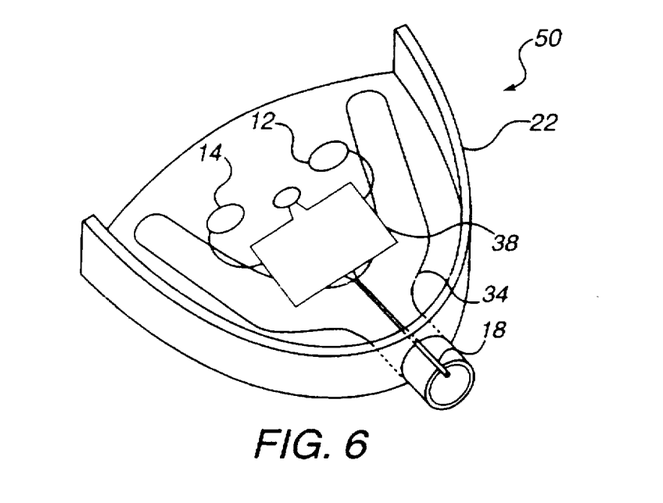
FIG. 6 is a plan view of a hybrid intraoral-extraoral embodiment of the present invention.
Figure 7:
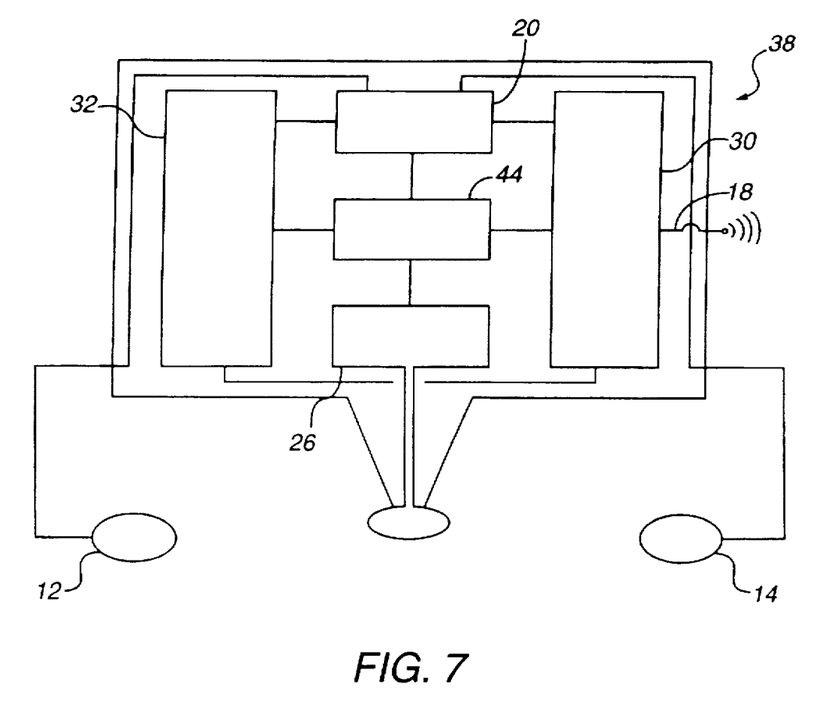
FIG. 7 is a schematic cross-section of an intraoral control unit for a hybrid intraoral-extraoral embodiment of the present invention.
Figure 8:
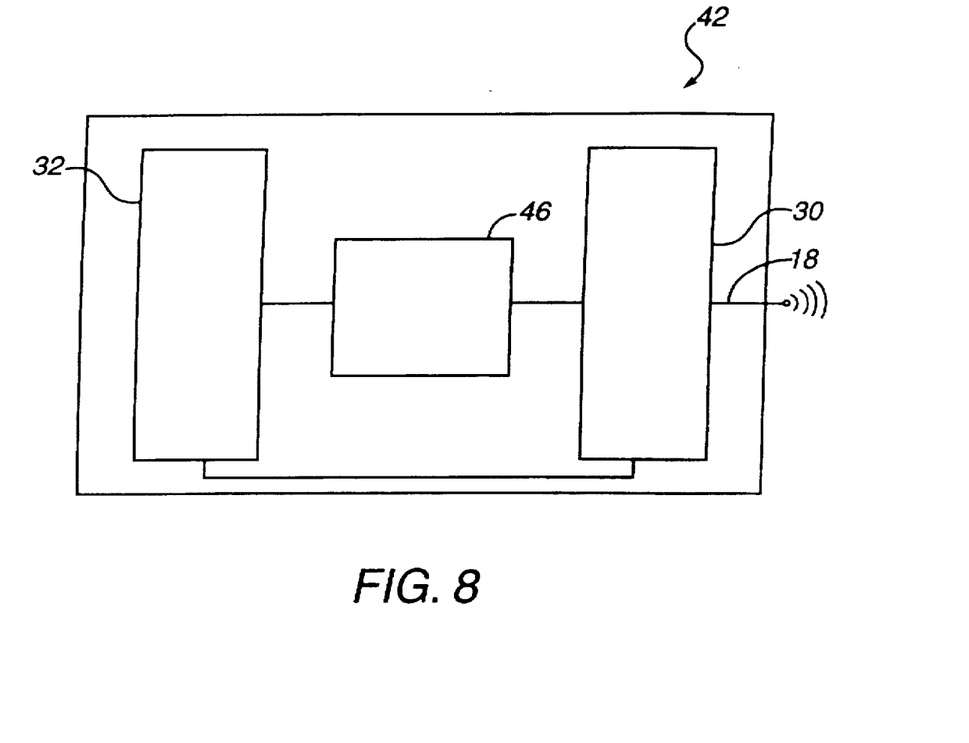
FIG. 8 is a schematic cross-section of an extraoral control unit for a hybrid intraoral-extraoral embodiment of the present invention.

In a third embodiment, the functionality provided by intraoral control unit 16 in the first embodiment is apportioned between intraoral control unit 38 and extraoral control unit 42. Intraoral control unit 38 resides in the user's mouth and extraoral control unit 42 is entirely external to the user's mouth, as in the second embodiment. In this embodiment, the stimulator comprises a mouthpiece unit 50, as depicted in FIG. 6; extraoral control unit 42, as depicted in FIG. 8; and a communication element 18, as depicted in FIGS. 6, 7 and 8. Utilization of both intraoral and extraoral units can effect a compromise between the advantages of an entirely intraoral device and the advantages of an entirely extraoral device and achieve other advantages, some yet to be discovered.

For this implementation, the intraoral and extraoral control units 38 and 42 can be operably connected by way of a tangible communication element 18, e.g., a coaxial cable. Optionally, communication between extraoral control unit 42 and intraoral control unit 38 can be effected with an intangible communication element 18, e.g., electromagnetic signals that travel through the space between intraoral control unit 38 and extraoral control unit 42, in which case each of the intraoral and extraoral control units 38 and 42 comprises an electromagnetic signal transmitter, receiver or transceiver, e.g., a radio signal transceiver. To achieve two-way communication between the two control units 38 and 42, each of the control units 38 and 42 comprises an electromagnetic signal transceiver.

By utilizing electromagnetic signals for communication, the advantages of an extraoral unit can be achieved, while maintaining the mobility of the user. Further, the intraoral and extraoral units 38 and 42 can be at an arbitrary distance from each other. For example, if intraoral control unit 38 were in the southern hemisphere of the Earth and extraoral control unit 42 in the northern hemisphere, communication between the two units 38 and 42 could be effected via satellite. Other telemedicine configurations are possible.

FIGS. 7 and 8 are schematic diagrams, which depict internal components of intraoral control unit 38 and extraoral control unit 42, respectively, for the third embodiment. Unless otherwise indicated below, the above description of the internal components of intraoral control unit 16 for the first embodiment applies to the internal components of intraoral and extraoral control units 38 and 42 for the third embodiment. Unlike intraoral control unit 16, however, intraoral and extraoral control units 38 and 42 further comprise a communication element 18 and, optionally, electromagnetic transmitters, receivers or transceivers.

Referring to FIG. 7, an electromagnetic signal transceiver 30 is operably connected to (1) electrical signal generator 20 for communicating control signals from extraoral control unit 42 to electrical signal generator 20, (2) controller 44 for exchanging control information with extraoral control unit 42 and (3) sensor 26 for communicating sensor information signals from sensor 26 to extraoral control unit 42. Referring to FIG. 8, an electromagnetic signal transceiver 30 is operably connected to a controller 46 for exchanging control information with intraoral control unit 38.

Of course, the internal components of intraoral and extraoral control units 38 and 42 can be modified, depending on how the functionality of the stimulator is apportioned between intraoral and extraoral control units 38 and 42. For example, instead of having intraoral and extraoral control units 38 and 42 share the control function, as depicted in FIGS. 7 and 8, extraoral control unit 42 can exercise full control. In that case, (1) controller 44 is omitted from intraoral control unit 38, (2) controller 46 in extraoral control unit 42 assumes full control, (3) extraoral control unit 42 receives sensor information from intraoral control unit 38 and (4) controller 46 communicates an appropriate control signal to electrical signal generator 20 in response to the sensor information. Additional variations are possible.

The effectiveness of the stimulator varies with the placement of the electrodes within the mouth of the user. A preferred intraoral position for each electrode can be determined by carrying out the following steps: (1) positioning the electrode in a position on the first anatomical structure, (2) applying an electrical signal to the electrode, (3) measuring a physiological response of the user to the application of the electrical signal, (4) recording the position and corresponding physiological response in a storage device, (5) varying the position based on information recorded in the storage device, if the response is not minimally satisfactory, and (6) repeating steps 1 through 5, inclusive, until a minimally satisfactory response is measured.

Similarly, a preferred characteristic of the electrical signal that is applied inside the mouth of the user by the stimulator can be determined by carrying out the following steps: (1) positioning the stimulator in the mouth of the user, (2) applying an electrical signal having a characteristic to the an electrode, (3) measuring a physiological response of the user to the application of the electrical signal, (4) recording the characteristic and corresponding physiological response in a storage device, (5) varying the characteristic based on information recorded in the storage device, if the response is not minimally satisfactory, and (6) repeating steps 1 through 5, inclusive, until a minimally satisfactory response is measured.

In one study of the present invention, a total of seven patients with histories of snoring and OSA participated. Each patient was supplied with a custom acrylic palatal appliance that contained two gold-plated electrodes for contacting the soft palate. The electrodes were activated by a waveform generator controlled by a laptop computer. The patients were monitored in a sleep lab for electroculogram (right and left), electromyogram (submental, intercostal and anterior tibialis), EEG ($C_4$-$A_1$, $C_3$-$A_2$ and $O_1$-FP), electrocardiogram, nasal and oral air flow (thermistor), thoracic and abdominal chest movement, and oxygen saturation (pulse oximeter). The voltage, duration, delay and wave form of the electrical stimulus were varied to determine if there was a window of parameters in which the stimulus was effective without causing arousal. To evaluate the effect on snoring, a microphone was suspended above the patients to detect snoring noises, onset and interruption, which were fed into the computer and recorded on a polysomnograph. Snoring noises caused activation of the electrical stimulus. A 250 msec, 3 ma stimulus in the range of 9–10 volts caused a significant decrease in snoring (p <0001, unpaired t-test) and was generally found to be effective in terminating individual snores without patient arousal.

Although we have illustrated and described a present preferred embodiment of the invention and variations thereon, the invention is not limited thereto but may be embodied otherwise within the scope of the following claims.

I claim:

1. An electromuscular stimulator for providing electrical stimulation to tissues within the mouth of a user, comprising:

a first electrode for making electrical contact with a first intraoral anatomical structure selected from the group consisting of a hard palate, a soft palate and a pharynx;

a second electrode for making electrical contact with a second intraoral anatomical structure;

a control unit operably connected to the first and second electrodes, the control unit comprising an electrical signal generator and further comprising a sensor for detecting the presence of a physiological condition; and an intraoral member for positioning the first and second electrodes intraorally relative to the first and second anatomical structures, respectively.

2. The stimulator of claim 1, wherein the first electrode is adapted to be permanently attached to the first anatomical structure.

3. The stimulator of claim 1, wherein the first electrode comprises a pliable electroconductive material.

4. The stimulator of claim 1, wherein the first electrode comprises a carbon-impregnated metal.

5. The stimulator of claim 1, wherein the first electrode comprises an electroconductive carbon-impregnated plastic.

6. The stimulator of claim 1, wherein the first electrode comprises an electroconductive rubber.

7. The stimulator of claim 1, wherein the first electrode comprises an electroconductive gel.

8. The stimulator of claim 1, wherein the first and second anatomical structures comprise the same anatomical structure.

9. The stimulator of claim 1, wherein the control unit is sized to fit within the mouth of the user during operation.

10. The stimulator of claim 9, wherein the control unit is hermetically sealed.

11. The stimulator of claim 1, wherein the control unit is microminiaturized.

12. The stimulator of claim 1, wherein the control unit is capable of residing outside of the mouth of the user during operation.

13. The stimulator of claim 1, wherein the electrical signal generator comprises a pulse generator.

14. The stimulator of claim 1, wherein the electrical signal generator comprises a transcutaneous electrical nerve stimulator.

15. A method of determining a preferred characteristic of the electrical signal of the stimulator of claim 1, comprising the following steps:

a. positioning the stimulator in the mouth of the user;

b. applying an electrical signal having a characteristic to the first electrode;

c. measuring a physiological response of the user to the application of the electrical signal;

d. recording the characteristic and corresponding physiological response in a storage device;

e. varying the characteristic based on information recorded in the storage device, if the response is not minimally satisfactory; and f. repeating steps (b) through (e), inclusive, until a minimally satisfactory response is measured.

16. The stimulator of claim 1, wherein the electrical signal generator generates an electrical signal having a characteristic selected from the group consisting of shape, amplitude, length, frequency, intermittent mode and constant mode.

17. The stimulator of claim 16, wherein the characteristic is controlled by the user.

18. The stimulator of claim 1, wherein the electrical signal generator comprises a digital integrated circuit.

19. The stimulator of claim 1, wherein the positioning means comprises a denture-like plate.

20. The stimulator of claim 1, wherein the positioning means is capable of being molded by the user.

21. The stimulator of claim 1, wherein the positioning means is fixedly attached to the control unit.

22. The stimulator of claim 1, further comprising a connecting means for removably attaching the positioning means to a third anatomical structure.

23. The stimulator of claim 22, wherein the connecting means utilizes an adhesive.

24. The stimulator of claim 22, wherein the connecting means utilizes a clamping device.

25. The stimulator of claim 22, wherein the connecting means utilizes a suction device.

26. The stimulator of claim 22, wherein the third anatomical structure comprises a palate.

27. The stimulator of claim 22, wherein the third anatomical structure comprises a tooth.

28. The stimulator of claim 1, wherein the positioning means is disposable.

29. The stimulator of claim 1, wherein the sensor comprises electrodes that monitor electrical activity in a brain.

30. The stimulator of claim 1, wherein the sensor comprises electrodes that monitor electrical activity in an intraoral muscle.

31. The stimulator of claim 1, wherein the sensor comprises a chemical sensor that monitors an intraoral level of a gas selected from the group consisting of $CO_2$, $O_2$ and any hydrocarbon emitted from tissue.

32. The stimulator of claim 1, wherein the sensor comprises a force gauge that monitors the tone of an intraoral muscle.

33. The stimulator of claim 1, wherein the sensor comprises an air flow sensor that monitors intraoral air flow.

34. The stimulator of claim 1, wherein the sensor comprises a microphone that monitors intraoral sounds.

35. The stimulator of claim 1, wherein the control unit further comprises a controller operably connected to the electrical signal generator for activating the electrical signal generator.

36. The stimulator of claim 35, wherein the controller comprises a digital integrated circuit.

37. The stimulator of claim 1, wherein the control unit further comprises a controller operably connected to the sensor and operably connected to the electrical signal generator for activating the electrical signal generator in response to detection of the physiological condition.

38. The stimulator of claim 27, wherein the controller determines the type of electrical signal to be generated in response to the physiological condition.

39. The stimulator of claim 1, wherein the control unit further comprises a power supply.

40. The stimulator of claim 39, wherein the power supply is chemical-based.

41. The stimulator of claim 39, wherein the power supply comprises a battery.

42. The stimulator of claim 39, wherein the power supply comprises an external energy source.

43. The stimulator of claim 1, wherein the control unit comprises:
   an intraoral control unit;
   an extraoral control unit; and
   a communication element operably connecting the intraoral control unit to the extraoral control unit.

44. The stimulator of claim 43, wherein the communication element is an electromagnetic signal.

45. The stimulator of claim 44, wherein the electromagnetic signal is a radio frequency signal.

46. The stimulator of claim 43, wherein each of the intraoral control unit and the extraoral control unit further comprises an electromagnetic signal communication device selected from the group consisting of a transmitter, a receiver and a transceiver for communicating the electromagnetic signal between the intraoral control unit and the extraoral control unit.

47. The stimulator of claim 1, further comprising an air channel operatively connected to the positioning member and having an intraoral end and an extraoral end for providing free flow of air between the mouth of the user and ambient atmosphere.

48. The stimulator of claim 47, wherein said extraoral end of said air channel comprises a tube, and said intraoral end of said air channel comprises a plurality of tubes that merge into said extraoral end tube.

49. A method of determining a preferred intraoral position for the first electrode of the stimulator of claim 1, comprising the following steps:
   a. positioning the first electrode in a position on the first anatomical structure;
   b. applying an electrical signal to the first electrode;
   c. measuring a physiological response of the user to the application of the electrical signal;
   d. recording the position and corresponding physiological response in a storage device;
   e. varying the position based on information recorded in the storage device, if the response is not minimally satisfactory; and
   f. repeating steps (a) through (e), inclusive, until a minimally satisfactory response is measured.

50. A method of modifying the positioning means of the stimulator of claim 1 to effect an anatomical fit with the mouth of the user, comprising the following steps:
   softening the positioning means by placing it in a hot liquid bath;
   molding the positioning means into a desired anatomical shape; and
   cooling the device until it hardens.

51. An electromuscular stimulator for providing electrical stimulation to tissues within the mouth of a user, comprising:
   a first electrode for making electrical contact with a first intraoral anatomical structure selected from the group consisting of a hard palate, a soft palate and a pharynx;
   a second electrode for making electrical contact with a second intraoral anatomical structure;
   a control unit operably connected to the first and second electrodes;
   an intraoral member adapted to position the first and second electrodes intraorally relative to the first and second anatomical structures, respectively; and
   an air channel operably connected to said intraoral member and having an intraoral end and an extraoral end, said extraoral end comprising a tube adapted for location outside the user's mouth when in use to provide a free flow of air between the user and ambient atmosphere.

52. The stimulator of claim 51, wherein said intraoral end of said air channel comprises a plurality of tubes that merge into said extraoral end tube.

53. An electromuscular stimulator for providing electrical stimulation to tissues within the mouth of a user, comprising:

a first electrode for making electrical contact with a first intraoral anatomical structure selected from the group consisting of a hard palate, a soft palate and a pharynx;

a second electrode for making electrical contact with a second intraoral anatomical structure;

an intraoral member adapted to position the first and second electrodes intraorally relative to the first and second anatomical structures, respectively;

an intraoral control unit operably connected to the first and second electrodes; and an extraoral control unit in operable communication with the intraoral control unit through an electromagnetic signal;

wherein each of the intraoral control unit and the extraoral control unit further comprises an electromagnetic signal communication device selected from the group consisting of a transmitter, a receiver and a transceiver for communicating the electromagnetic signal between the intraoral control unit and the extraoral control unit.

54. The stimulator of claim 53, further comprising an air channel operably connected to said intraoral member and having an intraoral end and an extraoral end, said extraoral end comprising a tube adapted for location outside the user's mouth when in use to provide a free flow of air between the user and ambient atmosphere.

55. The stimulator of claim 54, wherein said intraoral end of said air channel comprises a plurality of tubes that merge into said extraoral end tube.

56. An electromuscular stimulator for providing electrical stimulation to tissues within the mouth of a user, comprising:

a first electrode for making electrical contact with a first intraoral anatomical structure selected from the group consisting of a hard palate, a soft palate and a pharynx;

a second electrode for making electrical contact with a second intraoral anatomical structure;

a control unit operably connected to the first and second electrodes, the control unit comprising an electrical signal generator and further comprising a controller operatively connected to the electrical signal generator for activating the electrical signal generator; and an intraoral member for positioning the first and second electrodes intraorally relative to the first and second anatomical structures, respectively.

57. The stimulator of claim 56, wherein the controller comprises a digital integrated circuit.

* * * * *